United States Patent
Wiener et al.

(10) Patent No.: US 6,908,472 B2
(45) Date of Patent: Jun. 21, 2005

(54) APPARATUS AND METHOD FOR ALTERING GENERATOR FUNCTIONS IN AN ULTRASONIC SURGICAL SYSTEM

(75) Inventors: Eitan T. Wiener, Cincinnati, OH (US); William T. Donofrio, Cincinnati, OH (US); Robert Alan Kemerling, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 513 days.

(21) Appl. No.: 09/954,795

(22) Filed: Sep. 17, 2001

(65) Prior Publication Data

US 2002/0077645 A1 Jun. 20, 2002

Related U.S. Application Data

(60) Provisional application No. 60/242,171, filed on Oct. 20, 2000.

(51) Int. Cl.$^7$ ............................................. A61B 17/32
(52) U.S. Cl. ....................................... 606/169; 604/22
(58) Field of Search ................................ 606/166, 169, 606/170, 171, 176–179

(56) References Cited

U.S. PATENT DOCUMENTS

| | | | | |
|---|---|---|---|---|
| 5,001,649 A | | 3/1991 | Lo et al. ..................... | 364/484 |
| 5,026,387 A | | 6/1991 | Thomas ....................... | 606/169 |
| 5,217,478 A | * | 6/1993 | Rexroth ....................... | 606/180 |
| 5,283,832 A | * | 2/1994 | Lockhart et al. ............. | 380/271 |
| 5,400,267 A | * | 3/1995 | Denen et al. ................. | 702/59 |
| 5,523,746 A | * | 6/1996 | Gallagher .................... | 340/5.61 |
| 5,688,235 A | * | 11/1997 | Sakurai et al. ................ | 604/22 |
| 5,728,130 A | | 3/1998 | Ishikawa et al. ............ | 606/185 |
| 6,066,135 A | | 5/2000 | Honda .......................... | 606/39 |
| 6,120,462 A | * | 9/2000 | Hibner et al. ................ | 600/566 |

FOREIGN PATENT DOCUMENTS

| | | |
|---|---|---|
| EP | 1 025 806 A1 | 8/2000 |
| WO | 95/03001 | 2/1995 |

* cited by examiner

*Primary Examiner*—Kevin T. Truong
*Assistant Examiner*—Victor X Nguyen

(57) ABSTRACT

The present invention provides a system for implementing surgical procedures which includes an ultrasonic surgical hand piece having an end-effector, a console having a digital signal processor (DSP) for controlling the hand piece, an electrical connection connecting the hand piece and the console, and a memory, such as an EEPROM (Electrically Erasable Programmable Read Only Memory), disposed in the electrical connection. The console sends a drive current to drive the hand piece which imparts ultrasonic longitudinal movement to the blade. The console reads the memory and authenticates the hand piece for use with the console if particular or proprietary data are present in the memory. Moreover, to prevent errors in operating the hand piece, the memory can store certain diagnostic information which the console can utilize in determining whether the operation of the hand piece should be handicapped or disabled. Furthermore, the memory can be used to reprogram the console, if needed.

21 Claims, 11 Drawing Sheets

APPARATUS AND METHOD FOR ALTERING GENERATOR FUNCTIONS IN AN ULTRASONIC SURGICAL SYSTEM

RELATED APPLICATIONS

The present application relates to, and claims priority of, U.S. Provisional Patent Application Ser. No. 60/242,171 filed on Oct. 20, 2000 and entitled EEPROM TO ENABLE/DISABLE GENERATOR FUNCTIONS IN AN ULTRASONIC SURGICAL HAND PIECE, which is incorporated herein by reference.

BACKGROUND OF THE INVENTION

1. Field of the Invention

The present invention generally relates to an apparatus & method for altering generator functions in an ultrasonic surgical system and, more particularly, to an ultrasonic system for providing information to a generator from an ultrasonic surgical instrument.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering, which increases the risk of spreading infectious diseases to operating room personnel. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop that includes a voltage controlled oscillator, a frequency divider, a power switch, a match net and a phase detector, stabilizes the frequency applied to the hand piece. A microprocessor controls the amount of power by sampling the frequency current and voltage applied to the hand piece, because these parameters change with load on the blade.

The power versus load curve in a generator in a typical ultrasonic surgical system, such as that described in the Thomas patent has two segments. The first segment has a positive slope of increasing power, as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, keeps monitoring of the transducer current to voltage phase angle and maintains the transducer resonating by driving it at the resonance frequency. A key function of such systems is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot hop over other resonance modes or make any heuristic decisions such as what resonance/s to skip or lock onto and ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

Some limited diagnostic tests performed in the past involve sending a signal to the transducer to cause the blade to move and the system to be brought into resonance or some other vibration mode. The response of the blade is then determined by measuring the electrical signal supplied to the transducer when the system is in one of these modes. The ultrasonic system described in U.S. application Ser. No. 60/693,621 and filed on Oct. 20, 2000 which is incorporated herein by reference possesses the ability to sweep the output drive frequency, monitor the frequency response of the ultrasonic transducer and blade, extract parameters from this response, and use these parameters for system diagnostics. This frequency sweep and response measurement mode is achieved via a digital core such that the output drive frequency can be stepped with high resolution, accuracy, and repeatability not existent in prior art ultrasonic systems.

However, the prior art systems do not provide for authentication of the use of the hand piece with the console. Furthermore, conducting diagnostic and performance tests in the prior art systems is cumbersome. Reprogramming or upgrading of the console in the prior art systems is also burdensome, since each console needs to be independently tested and upgraded. In addition, the prior art system do not allow operation of the console with varied driving current and output displacement, depending on the type and output ability of hand piece in operation with the console. Therefore, there is a need in the art for an improved system for implementing surgical procedures which overcomes these and other disadvantages in the prior art.

SUMMARY OF THE INVENTION

The present invention provides a system for implementing surgical procedures which includes an ultrasonic surgical hand piece having an end-effector, a console having a digital signal processor (DSP) for controlling the hand piece, an electrical connection connecting the hand piece and the console, and a memory device such as an EEPROM (Electrically Erasable Programmable Read Only Memory) disposed in the electrical connection or the hand piece. Data, in the form of a data string which identifies the hand piece and generator performance characteristics, is stored in the memory device. During initialization of the system, the console sends an interrogation signal to the hand piece to obtain a readout of the memory. As the console reads the memory, the hand piece is authenticated for use with the console if the proper data is present. The hand piece is not authenticated for use with the console if the data is not present or is not correct. In a particular embodiment of the invention, the data is an encrypted code, where the hand piece is authenticated for use with the console by decoding a corresponding encryption algorithm resident in the console and providing a responding data pattern.

Moreover, to prevent errors in operating the hand piece, the memory can store certain diagnostic information which the console can utilize in determining whether the operation of the hand piece should be handicapped or disabled. For instance, the memory can store information such as limits on the time that the hand piece is active, the number of activations within a time period, the number of defective blades used, operating temperature, and other limits. Those limits stored in the memory can be re-initialized accordingly based on various operational conditions of the hand piece.

The memory can also be used to reprogram or upgrade the console, if needed. For example, new hand pieces are issued periodically as new system functionality is achieved. When such a new hand piece is connected, the system perform diagnostic tests to determine whether a reprogram or upgrade of the console is needed. If it is determined that a reprogram or upgrade is needed, the console reads the memory located in the electrical connection or hand piece where a reprogram or upgrade code is stored. Using the reprogram or upgrade code read from the memory, the console is reprogrammed or upgraded accordingly. Therefore, the consoles in the field can be upgraded automatically without having to return them to the manufacturer or to send a service technician to the console. In a particular embodiment, the memory is a non-volatile memory can be plugged into the electrical connection or hand piece.

The memory can also store energy level information and corresponding output displacement for driving the particular hand piece. By reading the energy level information, the console can drive the hand piece according to the output displacement which is best for that hand piece.

In addition, the memory can store frequency sweep information including the nominal resonant frequency, and start and stop sweep points for effecting a frequency sweep. Upon reading of the frequency sweep information stored in the memory, the console effects a frequency sweep in the indicated frequency range for detecting a resonant frequency for operating the hand piece.

In accordance with the invention, a method is provided for implementing procedures in a system including an ultrasonic surgical hand piece having an end-effector, a console having a digital signal processor (DSP) for controlling the hand piece, an electrical connection connecting the hand piece and the console, and a memory disposed in the electrical connection or hand piece. The method according to the invention includes reading information stored in the memory, determining whether particular or proprietary data are present in the memory, authenticating use of the hand piece with the console if the proprietary data are present, sending a drive current to drive the hand piece, and imparting ultrasonic movement to the end-effector of the hand piece according to information in the memory. In a particular embodiment, the method according to the invention also includes decoding an encryption algorithm in the console, and providing a responding data pattern, where the data is an encrypted code.

In a further embodiment, the method according to the invention includes instructing the hand piece to operate in a handicap mode if the temperature of the hand piece exceeds a handicap limit, and disabling the hand piece if the temperature of the hand piece exceeds a disable limit. The method according to the invention can also include instructing the hand piece to operate in a handicap mode if the number of defective blades found in a time period of operating the hand piece exceeds a handicap limit, and disabling the hand piece if the number of defective blades found in the time period exceeds a disable limit. The method according to the invention can further include instructing the hand piece to operate in a handicap mode if the time the hand piece has been active exceeds a handicap limit, and disabling the hand piece if the number of defective blades found in the time the hand piece has been active exceeds a disable limit. The method according to the invention can include further steps of operating the hand piece in a handicap mode if the number of activations for the hand piece, and/or the number of activations within a time period, exceed a handicap limit, and disabling the hand piece if the number of activations for the hand piece within the time period exceeds a disable limit. The handicap and disable limits stored in the memory can be re-initialized based on varied operational conditions of the hand piece.

In an additional embodiment, the method according to the invention also includes determining whether a reprogramming or upgrade of the console is needed, reading a reprogram or upgrade code stored in the memory and reprogramming the console using the reprogram or upgrade code, if it is determined that a reprogram or upgrade of the console is needed.

Moreover, the method according to another embodiment of the invention further includes reading energy level information stored in the memory, and driving the hand piece according to a corresponding output displacement, where the energy level information stored in the memory is correlated with corresponding output displacement for driving the particular hand piece. In yet another embodiment, the method according to the invention also includes reading a nominal resonant frequency, a start sweep point and a stop sweep point delimiting a frequency range from the memory, effecting a frequency sweep in the frequency range, and detecting a resonant frequency for operating the hand piece. Alternatively, the frequency range information stored in the memory can be a nominal resonant frequency, a bias amount and a margin amount, where the frequency range for the frequency sweep is calculated based on the nominal resonant frequency, the bias amount and the margin amount.

BRIEF DESCRIPTION OF THE DRAWINGS

The foregoing and other advantages and features of the invention will become more apparent from the detailed description of the preferred embodiments of the invention given below with reference to the accompanying drawings in which.

DETAILED DESCRIPTION OF THE PREFERRED EMBODIMENTS

Figure 1:
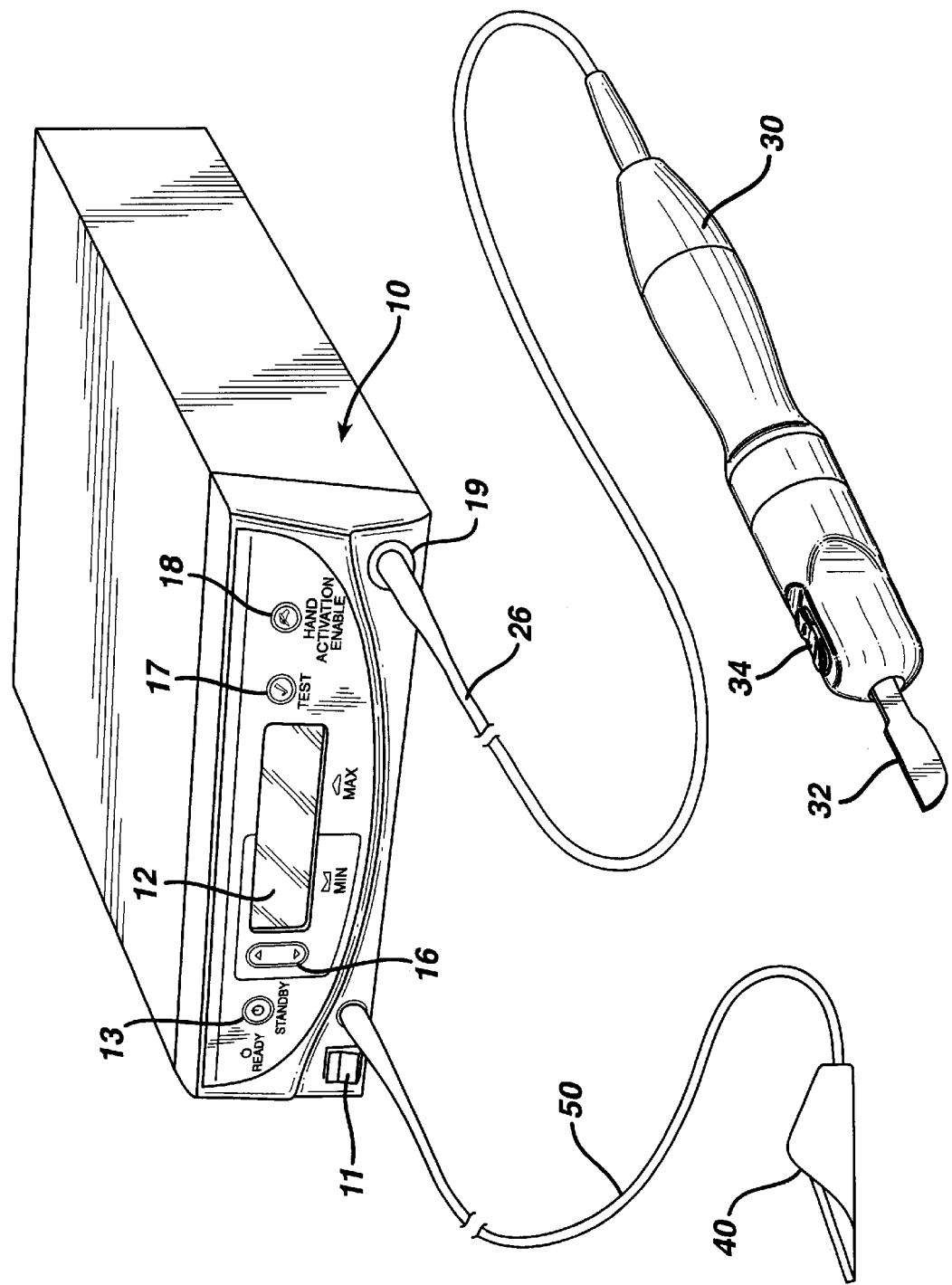
FIG. 1 is an illustration of a console for an ultrasonic surgical cutting and hemostasis system, as well as a hand piece and foot switch in which the method of the present invention is implemented.

FIG. 1 is an illustration of a system for implementing surgical procedures according to the invention. By means of a first set of wires in cable 20, electrical energy, i.e., drive current, is send from the console 10 to a hand piece 30 where it imparts ultrasonic longitudinal movement to a surgical device, such as a sharp end-effector 32. This blade can be used for generally simultaneous dissection and cauterization of tissue. The generator in console 10 drives the hand piece 30 such that the ultrasonically tuned blade 32 mounted on the proximal end thereof vibrates and in turn is used for cutting and coagulation in open or laparoscopic surgical procedures. The hand piece 30 is a hand-held device that includes an ultrasonic resonator or transducer that converts the appropriate electrical signals supplied by the generator in console 10 into mechanical vibrations for vibrating the frequency-tuned blade 32. The supply of ultrasonic current to the hand piece 30 may be under the control of a switch 34 located on the hand piece 30, which is connected to the generator in console 10 by a wire in cable 26 via the electrical connection 19. The generator may also be controlled by a foot switch 40, which is connected to the console 10 by another cable 50. Thus, in use a surgeon may apply an ultrasonic electrical signal to the hand piece 30, causing the blade to vibrate longitudinally at an ultrasonic frequency, by operating the switch 34 on the hand with his finger which is activated by pressing button 18, or by operating the foot switch 40 with his foot.

In a specific embodiment according to the invention, the button 18 is a set of twin rocker switches which are generally 180 degrees apart from each other. Each rocker switch in the button set 18 can signal to the generator console 10 for delivering power to the transducer in the hand piece 30 at a minimum or maximum power levels. In addition, the foot switch 40 includes two paddles of the press-and-hold activation type, where the paddle on the left serves as the switch for activating power delivery at a minimum level, and the paddle on the right serves as the switch for activating power delivery at a maximum level.

The generator console 10 includes a liquid crystal display device 12, which can be used for indicating the selected cutting power level in various means such as percentage of maximum cutting power or numerical power levels associated with cutting power. The liquid crystal display device 12 can also be utilized to display other parameters of the system. A power switch 11 and power "on" indicator 13 are also provided on the console. Further, buttons and switches 16 to 17 control various other functions of the system may be located on the console front panel.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate or force applied by the surgeon to the blade, the nature of the tissue type, and the vascularity of the tissue.

Figure 2:
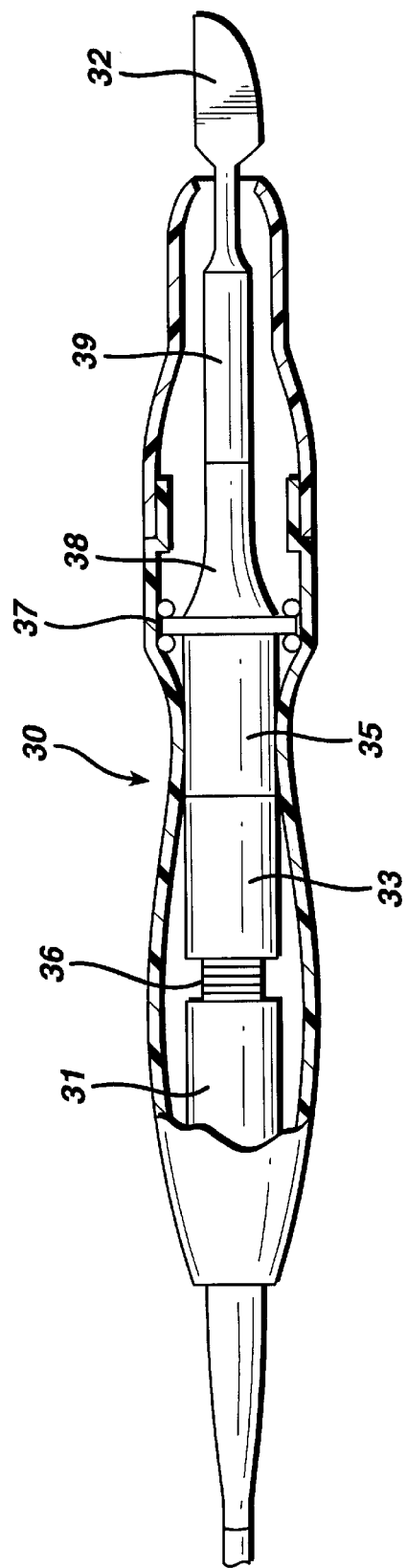
FIG. 2 is a schematic view of a cross section through the ultrasonic scalpel hand piece of the system of FIG. 1.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements having a motion null point at the center of the stack. It is mounted between two cylinders 31 and 33. In addition, a cylinder 35 is attached to cylinder 33, which is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion, with the center of the stack constituting a motionless node, when the transducer is driven at maximum current at the transducer's resonant frequency.

The parts of the hand piece are designed such that the combination will oscillate at generally the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32, preferably from 20 to 25 microns.

Figure 3A:
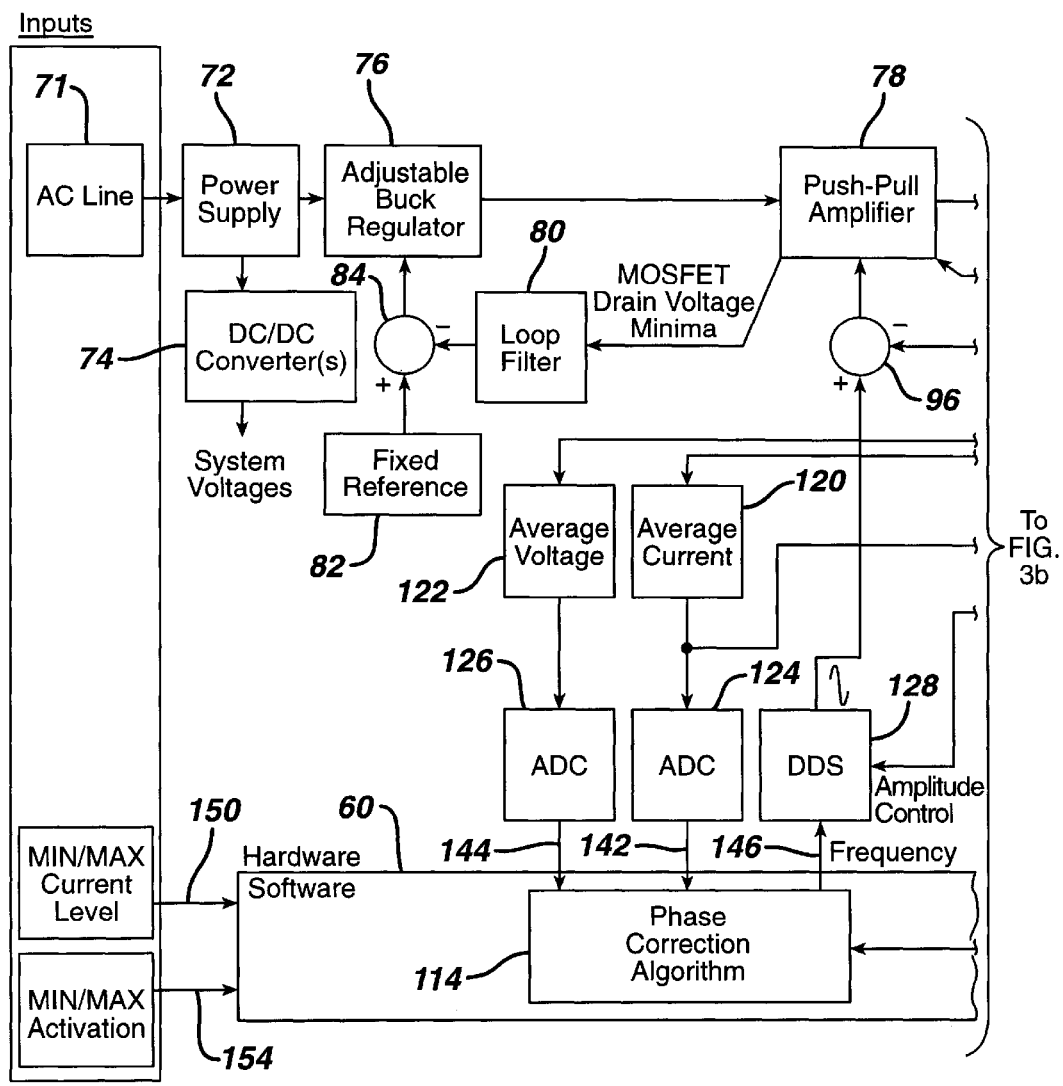
FIGS. 3A and 3B are block diagrams illustrating the system for the hand piece according to an embodiment of the present invention.
Figure 3B:
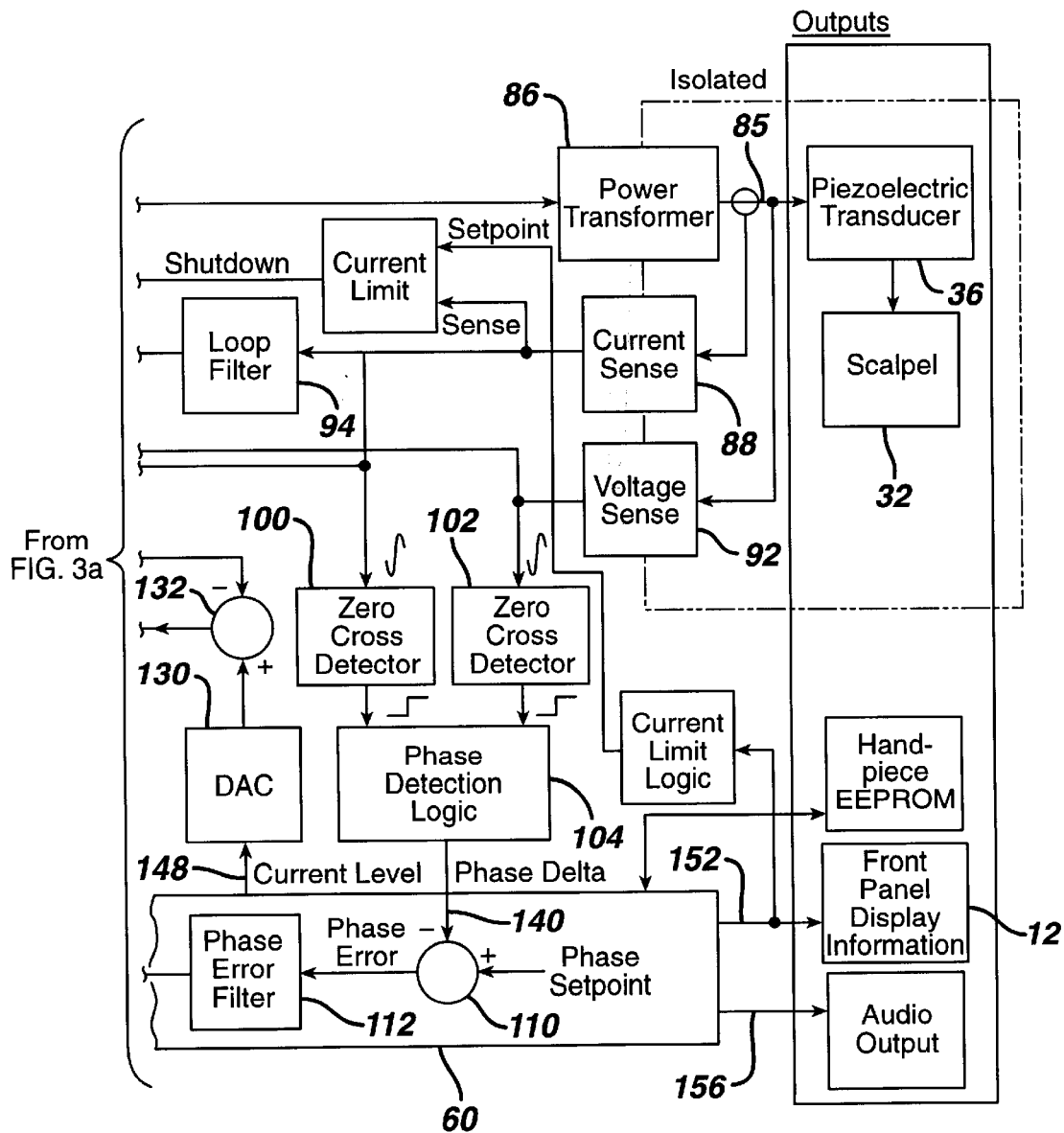

The system which creates the ultrasonic electrical signal for driving the transducer in the hand piece is illustrated in FIGS. 3A and 3B. This drive system is flexible and can create a drive signal at a desired frequency and power level setting. A DSP 60 or microprocessor in the system is used for monitoring the appropriate power parameters and vibratory frequency as well as causing the appropriate power level to be provided in either the cutting or coagulation operating modes. The DSP 60 or microprocessor also stores computer programs which are used to perform diagnostic tests on components of the system, such as the transducer/blade.

For example, under the control of a program stored in the DSP or microprocessor 60, such as a phase correction algorithm, the frequency during startup can be set to a particular value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is an undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility.

In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3B) to the console front panel display 12.

To actually cause the surgical blade to vibrate, the user activates the foot switch 40 or the hand piece switch 34. This activation puts a signal on line 154 in FIG. 3A. This signal is generally effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

As described herein with respect to FIGS. 2, 3A and 3B and in the related U.S. application Ser. No. 09/693,621 and incorporated herein by reference, the parts of the hand piece 30 in operational mode are designed, as a whole, to oscillate at generally the same resonant frequency, where the elements of the hand piece 30 are tuned so that the resulting length of each such element is one-half wavelength or a multiple thereof. Microprocessor or DSP 60, using a phase correction algorithm, controls the frequency at which the parts of the hand piece 30 oscillate. Upon activation of the hand piece 30, the oscillating frequency is set at a startup value or nominal resonant frequency such as 50 kHz which is stored in memory. A sweep of a frequency range between a start sweep point and a stop sweep point is effected under the control of the DSP 60 until the detection of a change in impedance which indicates the approach to the resonant frequency. The change in impedance refers to the impedance of the hand piece and its transducers, which may be modeled by a parallel equivalent circuit for mathematically modeling the algorithm for controlling the operation of the hand piece 30 as described in the related U.S. application Ser. No. 09/693,621. The resonant frequency is the frequency at a point during the frequency sweep where the impedance of the equivalent circuit is at its minimum and the anti-resonant frequency is the frequency where the impedance is maximum. Phase margin is the difference between the resonant frequency and an anti-resonant frequency. A correlation between the phase margin and the output displacement of the hand piece 30 exists which can advantageously be used to control the displacement so that the hand piece 30 operates at its optimal performance level.

In order to obtain the impedance measurements and phase measurements, the DSP 60 and the other circuit elements of FIGS. 3A and 3B are used. In particular, push-pull amplifier 78 delivers the ultrasonic signal to a power transformer 86, which in turn delivers the signal over a line 85 in cable 26 to the piezoelectric transducers 36 in the hand piece. The current in line 85 and the voltage on that line are detected by current sense circuit 88 and voltage sense circuit 92. The current and voltage sense signals are sent to average voltage circuit 122 and average current circuit 120, respectively, which take the average values of these signals. The average voltage is converted by analog-to-digital converter (ADC) 126 into a digital code that is input to DSP 60. Likewise, the current average signal is converted by analog-to-digital converter (ADC) 124 into a digital code that is input to DSP 60. In the DSP the ratio of voltage to current is calculated on an ongoing basis to give the present impedance values as the frequency is changed. A significant change in impedance occurs as resonance is approached.

The signals from current sense 88 and voltage sense 92 are also applied to respective zero crossing detectors 100, 102. These produce a pulse whenever the respective signals cross zero. The pulse from detector 100 is applied to phase detection logic 104, which can include a counter that is started by that signal. The pulse from detector 102 is likewise applied to logic circuit 104 and can be used to stop the counter. As a result, the count which is reached by the counter is a digital code on line 140, which represents the difference in phase between the current and voltage. The size of this phase difference is also an indication of how close the system is operating to the resonant frequency. These signals can be used as part of a phase lock loop that cause the generator frequency to lock onto resonance, e.g., by comparing the phase delta to a phase set point in the DSP in order to generate a frequency signal to a direct digital synthesis (DDS) circuit 128 that drives the push-pull amplifier 78.

Further, the impedance and phase values can be used as indicated above in a diagnosis phase of operation to detect if the blade is loose. In such a case the DSP does not seek to establish phase lock at resonance, but rather drives the hand piece at particular frequencies and measures the impedance and phase to determine if the blade is tight.

Figure 4:
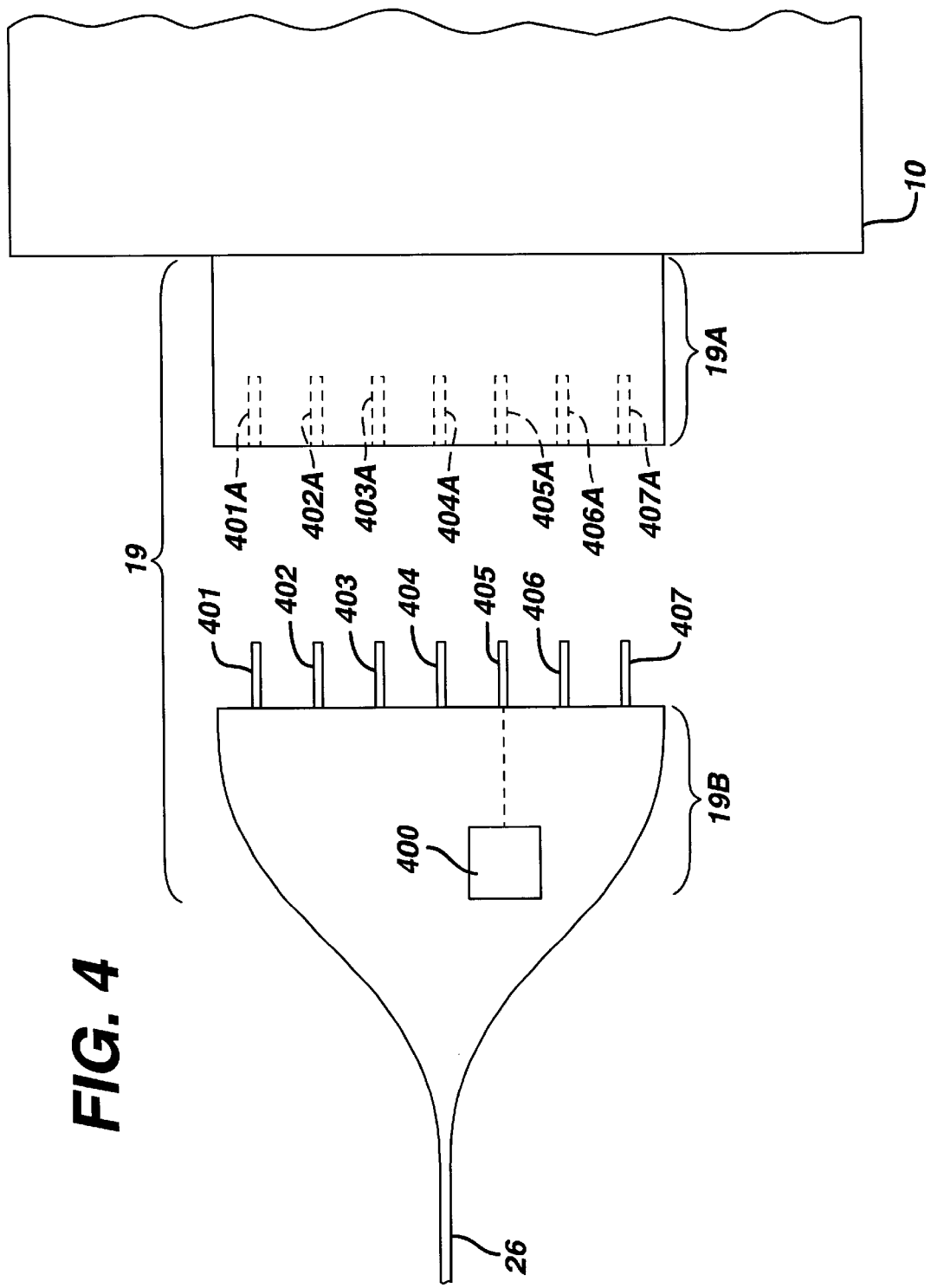
FIG. 4 is a diagram illustrating the electrical connection between the generator console and the ultrasonic surgical hand piece according to the invention in further detail.

FIG. 4 is a diagram that illustrates the electrical connection 19 between the console 10 and the hand piece 30 in further detail. According to a specific embodiment of the invention, the electrical connection 19, which can be a serial or parallel connection, is a male-female electrical connection set. It includes, on one end leading to the hand piece 30 via the cable 26, an electrical connector 19B with pins 401, 402, 403, 404, 405, 406 and 407, and on the other end a corresponding connector 19A leading to the console 10 and having receptacles 401A, 402A, 403A, 404A, 405A, 406A and 407A. These receptacles respectively receive pins 401, 402, 403, 404, 405, 406 and 407 of connector 19B. For engaging or disengaging the electrical connection 19, the connectors 19A and 19B only require simple act of connecting them by human hands, and need no additional tooling to engage or disengage them. The electrical connector 19B includes a memory 400 which is a non-volatile memory device that retains its data for subsequent usage even if power is removed therefrom, such as an electrically erasable programmable read only memory or EEPROM. The memory 400 is connected to pin 405 for transferring data to and from the console 10 at a direct current (DC) of generally 10 mA (milli-amperes).

With respect to the other pins, pin 401 is for delivering the "transducer high" signal for operating the transducer 36 in the hand piece 30 at a high power level, using an alternating current (AC) of generally 1 A (ampere). Pin 402 is for delivering the "transducer low" signal for operating the transducer 36 in the hand piece 30 at a low power level, also using an alternating current (AC) of generally 1 A. Pins 403 and 404 are for delivering hand-activation signals (e.g., by pressing button 18) to the hand piece 30, at an alternating current (AC) of generally 10 mA. Pin 406 is for delivering a general or common signal to the memory 400, at a direct current (DC) of generally 10 mA. Pin 407 is for delivering a signal which indicates the presence (or lack thereof) of the hand piece 30, also at a direct current (DC) of generally 10 mA.

The memory 400 is advantageously provided in the electrical connector 19B for reducing unneeded complexity in electrical isolation configurations which contribute to increases in costs, complications in cross-talk noise issues, and adversely affects the ergonomic performance of the hand piece 30. By placing the memory 400 in the electrical connector 19B, with adequate electrical isolation of the memory 400 circuitry, the human operator thereof, and the patient is readily achieved. Also, the number of wires in cable 26 can be reduced. However, if desired, the memory 400 can be located in the hand piece 30, but this is not preferred.

Figure 5:
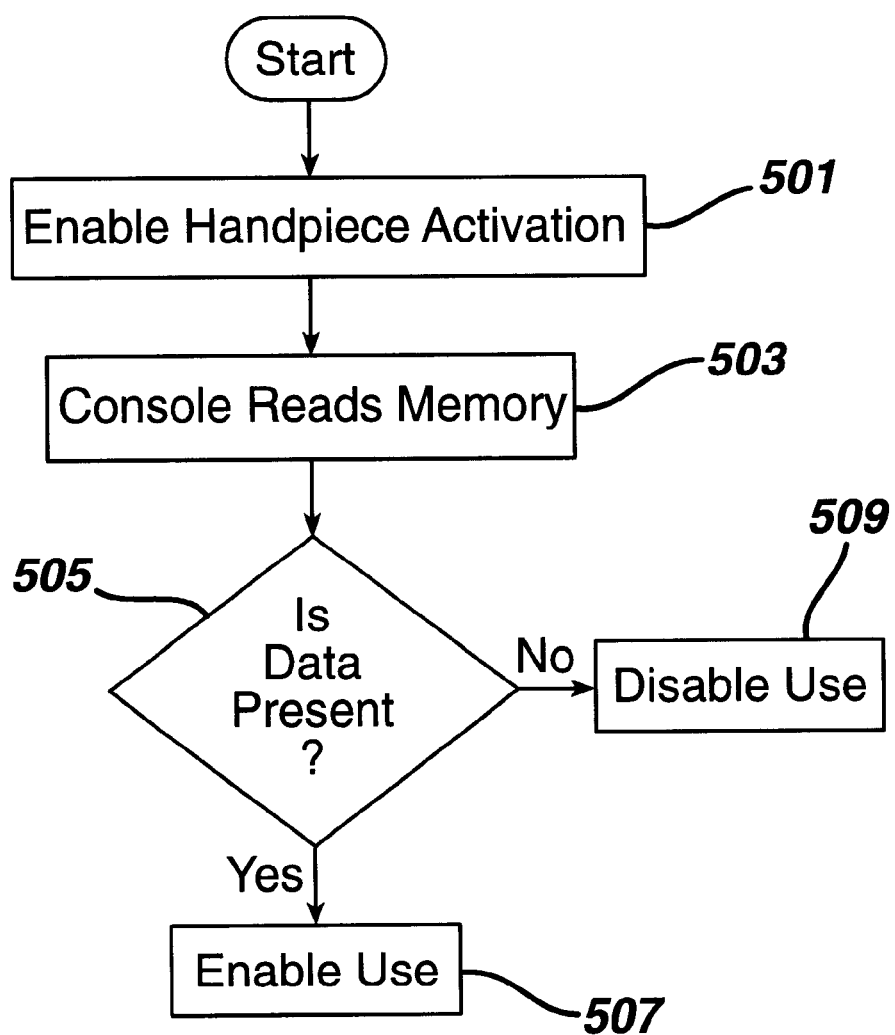
FIG. 5 is a flow diagram illustrating the operation of the non-volatile memory according to the invention as proprietary lockout for preventing inappropriate use of the ultrasonic surgical hand piece.

FIG. 5 is a flow diagram that illustrates the operation of the memory 400 as a proprietary lockout for preventing inappropriate use of the hand piece 30. The memory 400 can be utilized to prevent unauthorized, unintentional or inadvertent use of the hand piece 30 with the console 10. Inappropriate usage includes hazardous use, poor operational usage, or non-compatible use with the console 10.

In step 501, the hand piece 30 is activated, e.g., by pressing the button 18 on console 10 for hand-activation-enable of the hand piece 30. In step 503, console 10 then reads the memory 400 by accessing it via pin 405 in the electrical connection 19 at its mated position. In step 505, it is determined whether proprietary data (in the form of a data string) is present in the memory 400. The proprietary data, input into the non-volatile memory for all authorized hand pieces, are in digital or analog form. The proprietary data can also be a musical, speech, or sound effect in either digital or analog format. Having a proper proprietary data string in the memory 400 means that the use of the hand piece with console 10 is authorized or authenticated. The proprietary data can be copyrighted to protect against unlawful or unauthorized use of the hand piece. If the proprietary data are present in the memory 400, the hand piece 30 is enabled or activated by console 10 (step 507). If the proprietary data are not present in the memory 400 or an improper data string is present, the hand piece 30 is not enabled (step 509), and an error message appears on the display device 12 at the console 10 indicating unauthorized use.

In a specific embodiment according to the invention, when the console 10 reads the data in the memory 400, a cyclical redundancy check (CRC) is used to detect read errors and/or to authenticate the hand piece. A CRC is a mathematical method that permits errors in long runs of data to be detected with a very high degree of accuracy. Before data is transmitted over a phone, for example, the sender can compute a 32-bit CRC value from the data's contents. If the receiver computes a different CRC value, then the data was corrupted during transmission. Matching CRC values confirms with near certainty that the data was transmitted intact.

According to the CRC authentication technique, the entire block of data is treated as a long binary number which is divided by a conveniently small number and the remainder is used as the check value that is tacked onto the end of the data block. Choosing a prime number as the divisor provides excellent error detection. The number representing the complete block (main data plus CRC value) is always a multiple of the original divisor, so using the same divisor always results in a new remainder of zero. This means that the same division process can be used to check incoming data as is used to generate the CRC value for outgoing data. At the transmitter, the remainder is (usually) non-zero and is sent immediately after the real data. At the receiver, the entire data block is checked and if the remainder is zero, then the data transmission is confirmed.

An 8-bit CRC generator can be implemented in hardware, software or firmware in the memory 400. Firmware is the controller software for a hardware device, which can be written or programmed in a non-volatile memory (e.g., memory 400) such as an EEPROM or flash ROM (read only memory). The firmware can be updated with a flash program for detection and correction of bugs in the controller software or to improve performance of the hardware device. An exemplary EEPROM used in implementing the invention is the 256-bit DS2430A 1 wire device organized as one page of 32 bytes for random access with a 64-bit one-time programmable application register, which is a part of the IBUTTON™ family of hardware devices commercially available from DALLAS SEMICONDUCTOR™.

The following exemplary software code in "C" which is a commonly used programming language in the art, illustrates how the 8-bit CRC is calculated when reading the data in the memory 400 for authenticating use of the hand piece with console 10. Prior to the calculation of the CRC of a block of data, the 8-bit CRC is first initialized to zero. When console 10 reads the 8 bytes of the data in the memory 400, an 8-bit CRC is calculated for each of the 8 bytes of the data. If the resultant 8-bit CRC is equal to zero, then the use of the hand piece is with console 10 is authenticated, and the hand piece is enabled. If the resultant 8-bit CRC is not equal to zero, then the use of the hand piece with console 10 is not authenticated, the hand piece not enabled, and an error message appears on the display device 12 at console 10 indicating unauthorized use.

```
/*
FUNCTION
    mlan_CRC8
PASSED PARAMETERS
    'data' — data byte to calculate the 8 bit crc from
    'crc8' — the current CRC.
RETURN
    the updated 8 bit CRC.
/*
static uchar crc_table[] =
{
0, 94, 188,226, 97, 63,221, 131, 194,156,126, 32,163,253, 31, 65
157,195, 33,127,252,162, 64, 30, 95, 1,227, 189, 62, 96,130,220,
190,224, 2, 92,223,129, 99, 61,124, 34, 192,158, 29, 67,161,255,
70, 24,250,164, 39,121,155,197,132,218 56,102,229,187, 89, 7,
219,133,103,57,186,228, 6, 88, 25, 71, 165,251,120, 38,196,154,
101, 59,217,135, 4, 90,184,230,167,249, 27, 69,198,152,122,36,
248,166, 68, 26,153,199, 37,123, 58,100,134,216, 91, 5,231,185
140,210, 48,110,237,179, 81, 15, 78, 16,242,172, 47,113,147,205,
17, 79,173,243,112, 46,204,146,211, 141,111, 49,178,236, 14, 80,
175,241, 19, 77,206,144,114, 44,109, 51,209,143, 12, 82,176,238,
50,108,142,208, 83, 13,239,177,240,174, 76, 18,145,207, 45,115,
202,148,118, 40,171,245,23, 73, 8, 86,180,234,105, 55,213,139,
87, 9,235,181, 54,104,138,212,149,203, 41,119,244,170, 72, 22,
233,183, 85, 11,136,214, 52,106,43,117,151,201, 74,20,246,168,
116, 42,200,150, 21, 75,169,247,182,232, 10, 84,215,137,107,53
};
uchar mlan_CRC8(uchar data, uchar crc8)
{
return crc_table[crc8 ^ data];
}
```

Another exemplary software code is listed below for calculating a 16-bit CRC for the memory 400. Similarly, prior to the calculation of the CRC of a block of data, the 16-bit CRC is first initialized to zero. When console 10 reads the 16 bytes of the data in the memory 400, a 16-bit CRC is calculated for each of bytes 1 through 30 of the data, and the results are stored in bytes 31 and 32. After comparing the results, if the resultant CRC is equal to zero, then the use of the hand piece with console 10 is authenticated, and the hand piece is enabled. If the resultant CRC is not equal to zero, then the use of the hand piece with console 10 is not authenticated, the hand piece is not enabled, and an error message appears on the display device 12 at console 10 indicating unauthorized use.

```
/*
FUNCTION
    mlan_CRC16
PASSED PARAMETERS
    'data' — current word to add into the CRC
    'crc16' — the current value of the 16 bit CRC
RETURN
    new value of the 16 bit CRC
                                                        /*
static int oddparity[16] = {0, 1, 1, 0, 1, 0, 0, 1, 1, 0, 0, 1, 0, 1, 1, 0};
uint mlan-CRC16(uint data, uint crc16)
{
    data = (data ^ (crc16 & 0xff)) & 0xff;
    crc16>>=8
if (oddparity[data & 0xf] ^ oddparity[data >> 4])
    crc16 ^=0xc001;
data <<=6;
crc16 ^ = data;
data <<= 1;
crc16 ^ = data;
return crc16;
}
```

Furthermore, the data in the memory 400 can be an encrypted code which, when decoded by a corresponding encryption algorithm resident at console 10, provides a corresponding data pattern that serves to authenticate proper usage of the hand piece with the console. Encryption is achieved with algorithms that use a computer "key" to encrypt and decrypt messages by turning text or other data into an unrecognizable digital form and then by restoring it to its original form. The longer the "key," the more computing is required to crack the code. To decipher an encrypted message by brute force, one would need to try every possible key. Computer keys are made of "bits" of information of various length. For instance, an 8-bit key has 256 (2 to the eighth power) possible values. A 56-bit key creates 72 quadrillion possible combinations. If the key is 128 bits long, or the equivalent of a 16-character message on a personal computer, a brute-force attack would be 4.7 sextillion (4,700,000,000,000,000,000,000) times more difficult than cracking a 56-bit key. With encryption, unauthorized use of the hand piece with console 10 is generally prevented, with a rare possibility of the encrypted code being deciphered for unauthenticated use.

A unique identification (ID) number is registered and stored in the memory (e.g., memory 400) for every hand piece manufactured which is compatible for use with console 10. In a specific embodiment according to the invention, the memory 400 is the DS2430A 1 wire EEPROM device, commercially available from DALLAS SEMICONDUCTOR™, which stores a factory-lasered and tested 64-bit ID number for each hand piece manufactured. The ID number can be a model or model family number, in addition to being a unique serial number ID for each individual hand piece. This allows the generator console 10 to acknowlege its compatibility and useability therewith, without requiring a list of serial numbers for that model or model family. Foundry lock data in a hardware format and protocol is stored in the memory 400 to ensure compatibility with other products of generally the same communications protocol, e.g., the products of the MICROLAN™ protocol commercially available from DALLAS SEMICONDUCTOR™. This advantageously provides scalability for providing a system with additional surgical devices on a local area network (LAN) operating on generally the same communications protocol.

Figure 6:
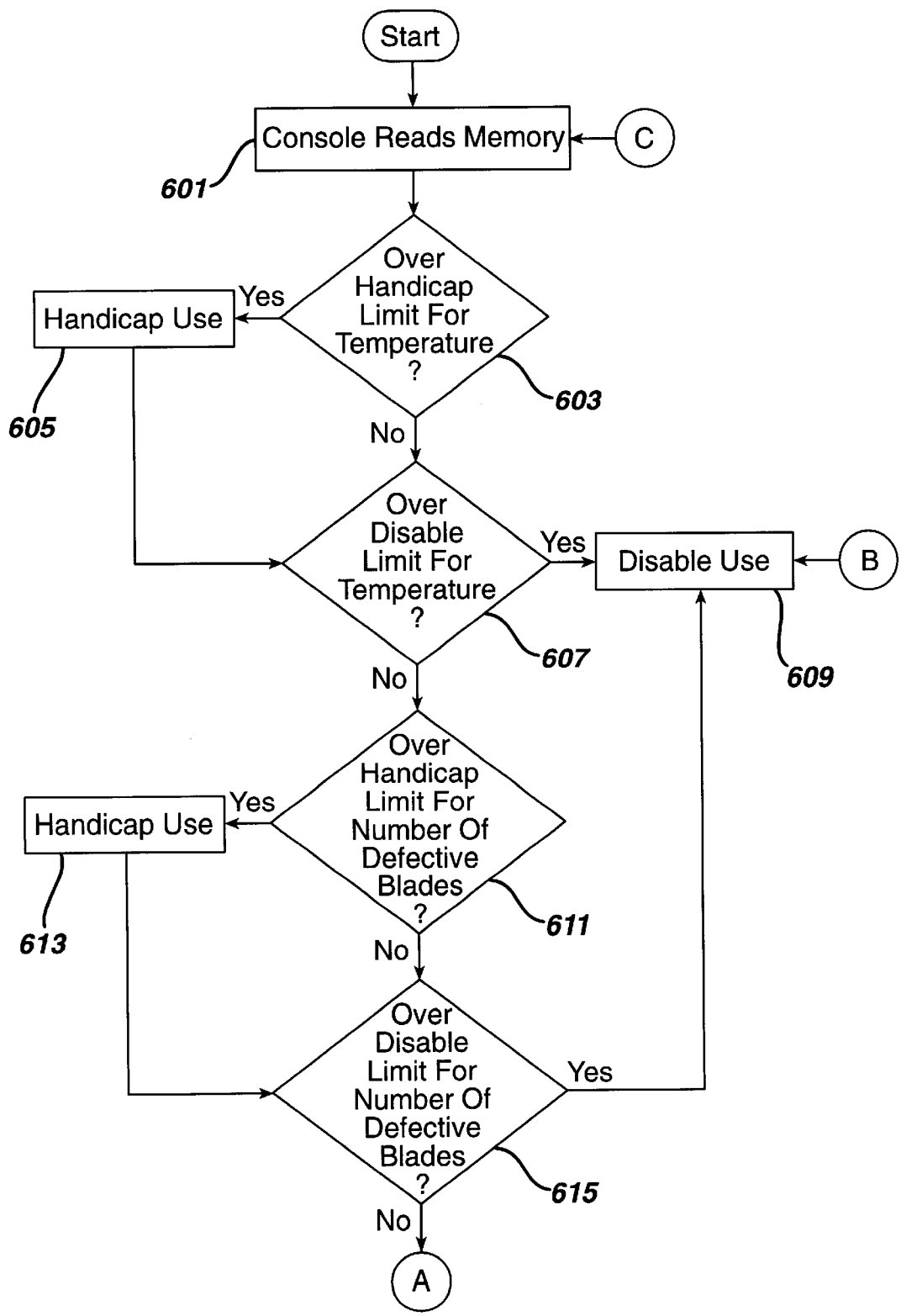
FIGS. 6 and 7 are flow diagrams illustrating the operation of the non-volatile memory according to the invention for error prevention when using the ultrasonic surgical hand piece.
Figure 7:
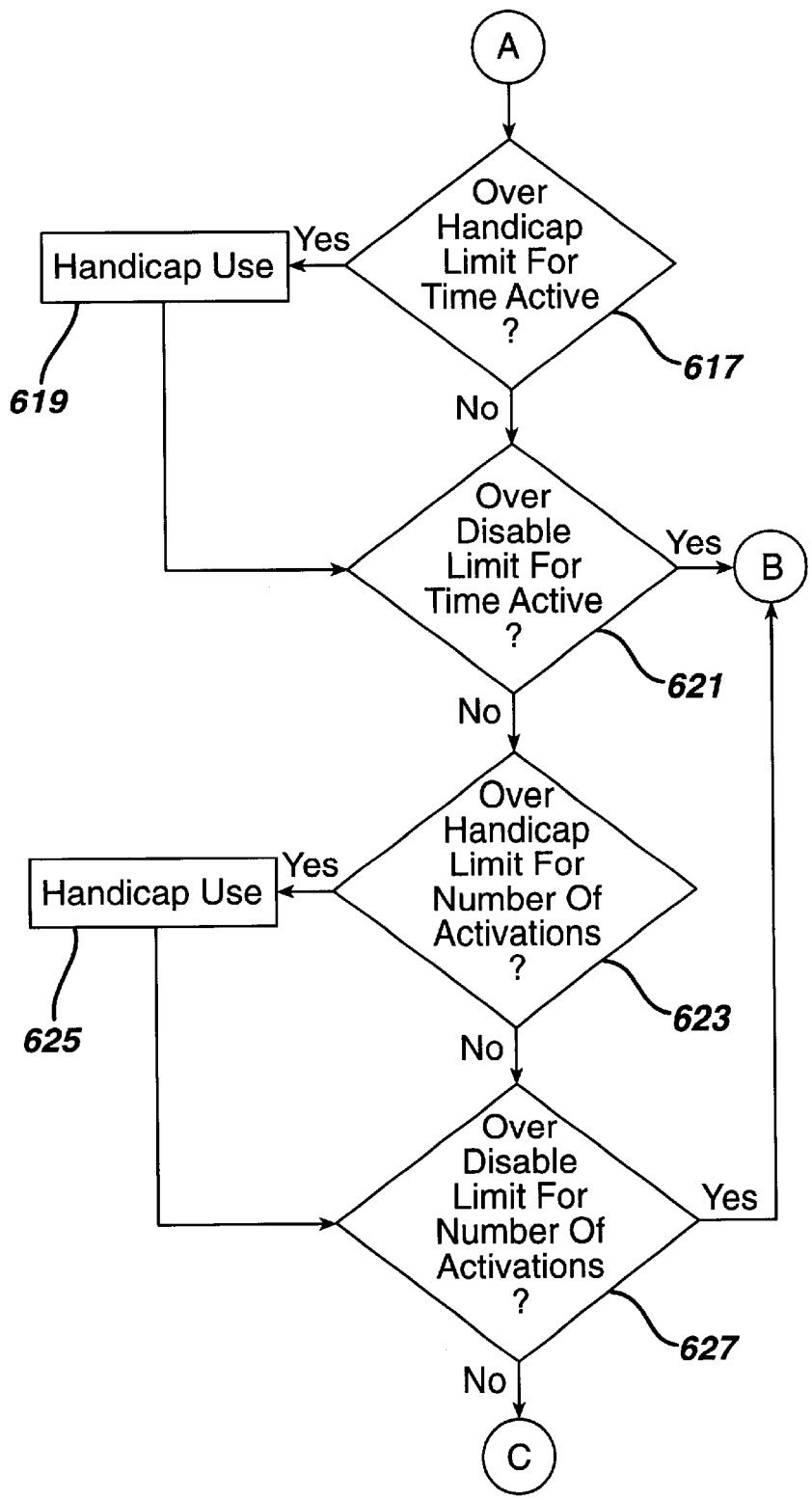

FIGS. 6 and 7 are flow diagrams that illustrate the operation of the memory 400 according to the invention for error prevention when using the hand piece 30 with console 10. To prevent errors in operating the hand piece 30, the memory 400 can store certain diagnostic information which console 10 can utilize in determining whether the operation of the hand piece 30 should be handicapped or disabled. For instance, the memory 400 can store information such as limits on the time that the hand piece is active, the number of activations within a time period, the number of defective blades used, temperature, and any other performance characteristics such as, for example, those listed in Table 1. Those skilled in the art can appreciate that other error prevention, diagnostic and performance characteristics can be stored in memory 400. Exemplary performance characteristics that can be stored in memory 400 (as shown in Table 1) include surgical device type information and revision data (row 1 in Table 1), current set point (row 2), transducer capacitance (row 3), cable capacitance (row 4), phase margin for the hand piece equipped with a test tip or end-effector (row 5), resonant frequency (row 6), remaining operating procedures (row 7), lower bound or threshold on operating frequency (row 8), upper bound or threshold on operating frequency (row 9), maximum output power (row 10), power control information and authorization (row 11), hand piece impedance (row 12), total on-time information at specific power levels (rows 13 and 14), hand piece enable/disable diagnostic information (row 15), hand piece error codes (row 16), temperature range and change data (rows 17, 18 and 19), current excess load limit (row 20), high impedance fault limit (row 21), and cyclical redundancy check (CRC) data (row 22).

Moreover, the memory 400 can store user-specific data such as username, internal tracking number, calibration schedule, and custom output performance. The user-specific data can be manipulated or programmed through the generator console 10 or initialized at the time the hand piece 30 is made at the factory.

TABLE 1

| | |
|---|---|
| 1 | Bits 1–3: Device Type<br>Bits 4–8: Revision |
| 2 | Current set point<br>$I_{setpoint}$ |
| 3 | Transducer Capacitance<br>$C_0$ |
| 4 | Cable Capacitance<br>$C_c$ |
| 5 | Phase margin with test tip<br>$Pm_0$ |
| 6 | Resonance frequency<br>$f_{ro}$ |
| 7 | Allowed Procedures Remaining |
| 8 | Lower bound on seek/lock frequency<br>(offset from $f_{ro}$)<br>$F_{lower\ bound}$ |

TABLE 1-continued

| | |
|---|---|
| 9 | Upper bound on seek/lock frequency<br>(offset from $f_{ro}$)<br>$f_{upper\ bound}$ |
| 10 | Maximum output power @ level 5 $W_{max}$. |
| 11 | Bit 1 Backside power curve control variable:<br>Capped Power = 1; Descending power = 0<br>Bit 2; Single cap at all levels = 1,<br>Different cap for each power level = 0<br>Bit 3: Hand piece Authorized Activation Flag.<br>Bits 4–8: Unused |
| 12 | Hand piece Impedance, Re \|Z\| |
| 13 | Total On-Time @ level 5 |
| 14 | Total on-Time @ level < 5 |
| 15 | Hand piece Diagnostics Enable/Disable Flags byte no. 1<br>Hand piece Diagnostics Enable/Disable Flags byte no. 2 |
| 16 | Hand piece error code 1 (newest)<br>Hand piece error code 2<br>Hand piece error code 3<br>Hand piece error code 4<br>Hand piece error code 5 (oldest) |
| 17 | $\Delta C_0$ Over Temp Entry |
| 18 | $\Delta C_0$ Over Temp Exit |
| 19 | $C_0$ Max Rate of Change |
| 20 | Current Excessive Load Limit |
| 21 | High Impedance with test tip fault limit |
| 22 | Data CRC |

According to a specific embodiment of the invention, once the hand piece 30 is activated for use, console 10 reads the memory 400 (step 601) for the diagnostic information. In step 603, console 10 determines whether the temperature of the hand piece 30 is over the handicap limit stored in the memory 400. If so, console 10 then instructs the hand piece 30 to operate in the handicap mode (step 605), e.g., operating below a certain speed or vibrational frequency or in a limited mode such as coagulation or cutting in order to avoid overheating, or in a non-limited mode with a specific vibrational annunciation. If not, the flow control goes to step 607, where console 10 determines whether the temperature of the hand piece 30 is over the disable limit stored in the memory 400. If so, console 10 disables the hand piece 30 (step 609). If not, the flow control goes to step 611, where console 10 determines whether the number of defective blades found within a time period of operating the hand piece 30 has exceeded the handicap limit stored in the memory 400. If so, console 10 then instructs the hand piece 30 to operate in the handicap mode (step 613), e.g., operating below a certain speed or vibrational frequency below the nominal vibrational displacement, or in a limited mode such as coagulation or cutting in order to decrease the incidences of blades 32 becoming defective. The handicap mode in step 613 is not necessarily the same as the handicap mode in step 605, depending on the optimal mode for operating the hand piece 30 under the circumstances with respect to steps 603 and 611.

If the number of defective blades found has not exceeded the handicap limit, the flow control is directed to step 615, where console 10 determines whether the number of defective blades found within a time period has exceeded the disable limit stored in the memory 400. If so, console 10 disables the hand piece 30 (step 609). If not, the control flow is directed, via step A, to step 617, where console 10 determines whether the time the hand piece 30 has been active has exceeded the handicap limit stored in memory 400. If so, console 10 instructs the hand piece 30 to operate in a handicap mode, e.g., operating below a certain speed or vibrational frequency, below the nominal vibrational displacement, or in a limited mode such as coagulation or cutting. The handicap mode in step 619 is not necessarily the same as the handicap mode in steps 605 or 613, depending on the optimal mode for operating the hand piece 30 under the circumstances with respect to steps 603, 611 and 617.

If the time the hand piece 30 has been active has not exceeded the handicap limit, the flow control is directed to step 621, where console 10 determines whether the time the hand piece has been active has exceeded the disable limit stored in the memory 400. If so, the control flow is directed, via step B, to step 609 where console 10 disables the hand piece 30. If not, the control flow goes to step 623, where console 10 determines whether the number of activations for the hand piece 30 within a time period has exceeded the handicap limit stored in memory 400. If so, console 10 instructs the hand piece 30 to operate in a handicap mode (step 625), e.g., operating below a certain speed or vibrational frequency, below the nominal vibrational displacement, or in a limited mode such as coagulation or cutting. The handicap mode in step 625 is not necessarily the same as the handicap mode in steps 605, 613 or 619, depending on the optimal mode for operating the hand piece 30 under the circumstances with respect to steps 603, 611, 617 and 623.

If the number of activations for the hand piece 30 within a time period has not exceeded the handicap limit, the flow control is directed to step 627, where console 10 determines whether the number of activations for the hand piece 30 within a time period has exceeded the disable limit stored in the memory 400. If so, the control flow is directed, via step B, to step 609 where console 10 disables the hand piece 30. If not, the control flow is directed, via step C, to step 601 from which the process steps according to this particular embodiment of the invention may be repeated upon subsequent users until the hand piece 30 is 20 caused to be disabled.

The disable limits and the handicap limits described herein with respect to FIGS. 6 and 7 may be of substantively different criteria for console 10 to determine the operational mode of the hand piece 30. The memory 400 may be re-initialized for different disable or handicap limits for varied operational conditions of the hand piece 30. Console 10 may likewise be re-initialized to operate on varied criteria for controlling the operational mode of the hand piece 30 based on the information stored in the memory 400.

In addition to the disable and handicap modes of operation, an alarm or alert mode can further be provided when certain criteria are met to alert and allow a human operator of the hand piece to take appropriate action to remedy the alerted operating condition.

Figure 8:
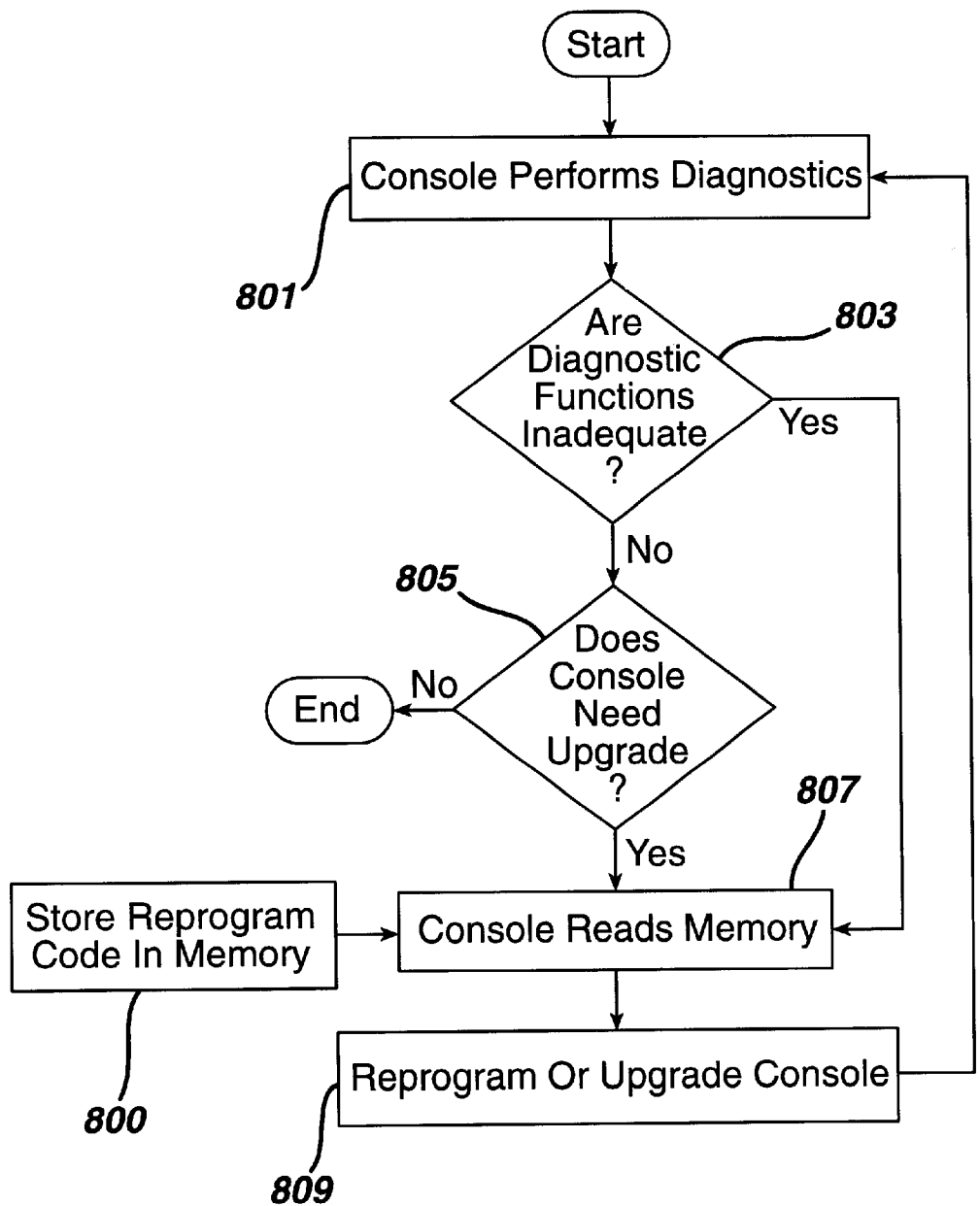
FIG. 8 is a flow diagram illustrating the operation of the non-volatile memory according to the invention for reprogramming or upgrading the console using the hand piece.

FIG. 8 is a flow diagram that illustrates the operation of the memory 400 according to the invention for reprogramming or upgrading console 10 using the hand piece 30. In step 801, console 10 performs diagnostic tests on the functions of the console. It is determined in step 803 whether any functions are deemed inadequate, e.g., functions that need to be altered, disabled or added. For example, the error prevention functions described herein with respect to FIGS. 6 and 7 may need to be added, or the handicap limits and operational modes may need to be re-initialized. If it is determined that certain functions are inadequate, the flow control is directed to step 807. In step 807, console 10 reads the memory 400 of the hand piece 30 where the reprogram code has been stored in step 800. Using the reprogram code read from the memory 400, the functions of console 10 are reprogrammed.

If it is determined in step 803 that the functions of console 10 are adequate or the memory has a newer version of the program, then the console 10 has, the flow control directed to step 805. It is determined in step 805 whether an upgrade is needed for console 10. If so, the flow control is directed to step 807. In step 807, console 10 reads the memory 400 of the hand piece 30 where the reprogram or upgrade code has been stored in step 800. Using the reprogram or upgrade code read from the memory 400, the functions of console 10 are reprogrammed and upgraded. For example, if console 10 is experiencing operational difficulties with a specific generation or version of the hand piece, an upgrade from the memory 400 instructs console 10 to allow its use with only newer versions or generations of the hand piece. The memory 400 can also store information including the manufacture date, design revision, manufacturing code, lot code or other manufacture-related information for a specific grouping of hand pieces according to generation or version having operational difficulties or defects, from which console 10 can be reprogrammed or upgraded to refuse activation for use with such hand pieces.

In an alternative embodiment according to the invention, the reprogram code can be stored in a non-volatile memory of a device other than the hand piece 30 with the memory 400. The non-hand piece device with the non-volatile memory can be plugged directly into the electrical connection 19 for upgrading or reprogramming console 10.

Moreover, the memory 400 can be utilized in adding an odometer function to the generator console 10 by keeping track of the number of uses performed for the hand piece 30 and/or the number of allowable uses remaining.

In addition to storing reprogram or upgrade code, the memory 400 can also store performance criteria for operating the hand piece 30 with console 10. For example, the memory 400 can store energy level information such as a maximum energy level for driving the particular hand piece 30, because, e.g., a relatively small hand piece may not be able to be driven, in terms of energy levels, as intensely as a relatively large hand piece for large-scale surgical procedures. Information correlating the energy levels for driving the hand piece 30 and the corresponding output displacement can also be stored in the memory 400. The console 10 reads the energy level information stored in the memory 400 and drives the hand piece 30 according to the corresponding output displacement. In addition to energy level information, driving signal characteristics, such as types of amplitude modulation and resonance frequency, can be stored in the memory 400. Using the information stored in the memory 400, the console 10 and the hand piece 30 can perform the error prevention described herein with respect to FIGS. 6 and 7, and the reprogramming or upgrade of console 10 described herein with respect to FIG. 8.

As described herein with respect to FIGS. 2 and 3 and in the related U.S. application Ser. No. 09/693,621 incorporated herein by reference, the parts of the hand piece 30 in the operational mode are designed, as a whole, to oscillate at generally the same resonant frequency, where the elements of the hand piece 30 are tuned so that the resulting length of each such element is one-half wavelength. Microprocessor or DSP 60, using a phase correction algorithm, controls the frequency at which the parts of the hand piece 30 oscillate. Upon activation of the hand piece 30, the oscillating frequency is set at a startup value or nominal resonant frequency such as 50 kHz which is stored in the memory 400 of the hand piece 30. A sweep of a frequency range between a start sweep point and a stop sweep point, whose values are also stored in the memory 400, is effected under the control of the DSP 60 until the detection of a change in impedance which indicates the approach to the resonant frequency. Having obtained the resonant frequency, the parts of the hand piece 30 are caused to oscillate at that frequency.

Figure 9:
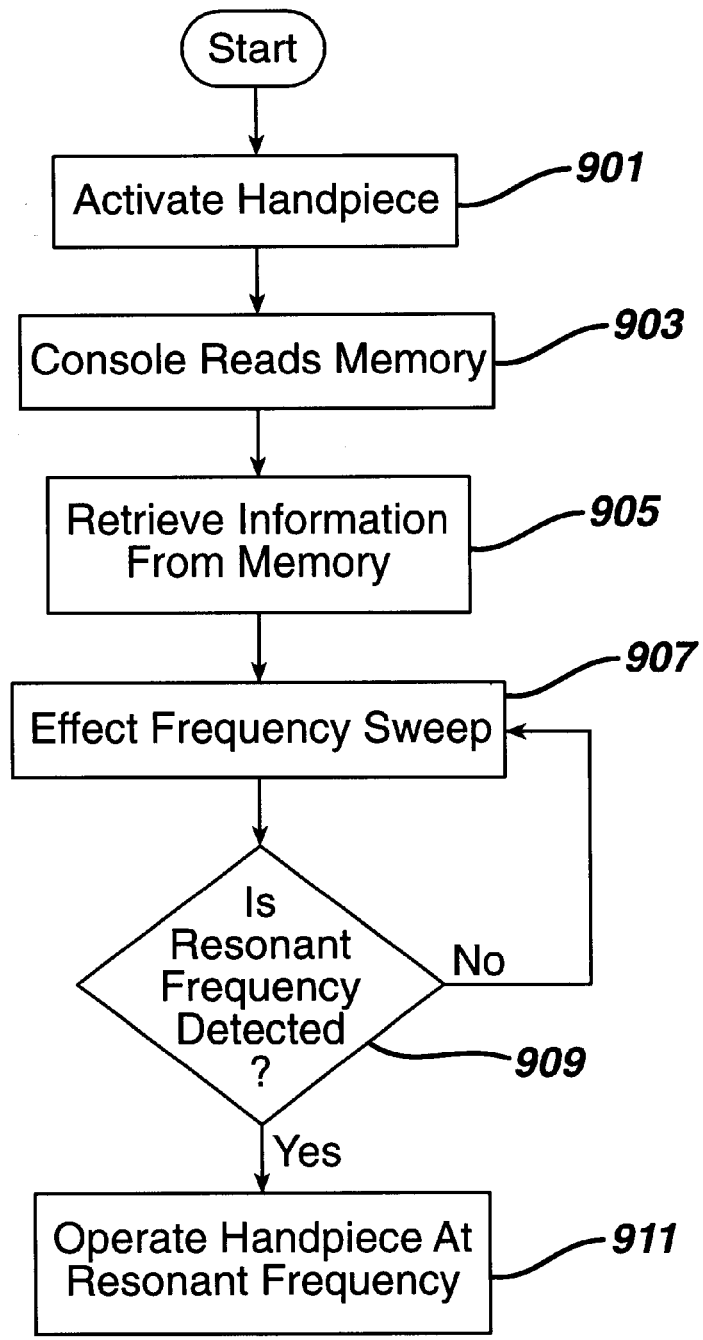
FIG. 9 is a flow diagram illustrating the operation of the ultrasonic surgical hand piece at a resonant frequency using information stored in the memory according to the invention.

FIG. 9 is a flow diagram that illustrates the operation of the hand piece 30 according to the invention at a resonant frequency using information stored in the memory 400. Once the hand piece 30 is activated (step 901), console 10 reads the memory 400 of the hand piece 30 (step 903) and retrieves the information needed for operating the hand piece 30 at the resonant frequency, including the nominal resonant frequency, a frequency range delimited by a start sweep point and a stop sweep point (step 905). A frequency sweep in that frequency range is effected under the control of the DSP 60 (step 907). Detection of the resonant frequency is effected in step 909. If the resonant frequency has not yet been detected, the control flow reverts back to step 907 where the frequency sweep is continued. Upon detection of the resonant frequency, the control flow is directed to step 911 where the parts of the hand piece 30 are caused to oscillate at that resonant frequency.

Figure 10:
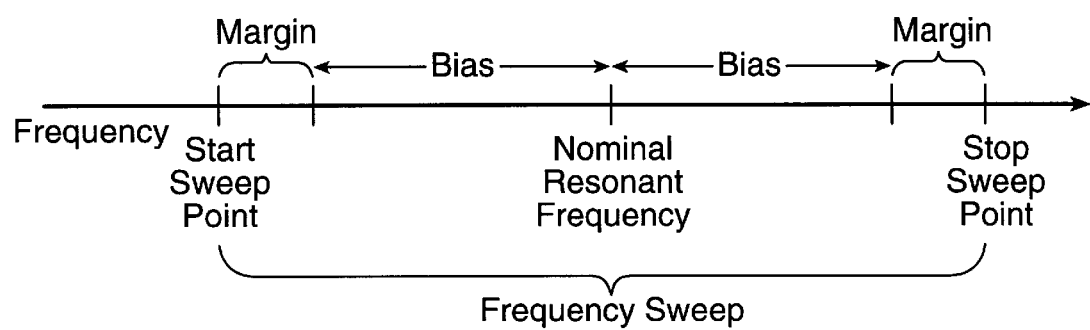
FIG. 10 is a diagram illustrating an alternative embodiment of the operation of the hand piece at a resonant frequency using information stored in the non-volatile memory according to the invention.

FIG. 10 is a diagram that illustrates an alternative embodiment of the operation of the hand piece 30 according to the invention at a resonant frequency using information stored in the memory 400. Instead of storing the start and stop sweep points of a frequency range for the frequency sweep, the memory 400 stores the nominal resonant frequency and a bias amount. The console 10 calculates the start and stop sweep points by subtracting and adding the bias amount from the nominal resonant frequency, respectively. A margin, which is a relatively small amount beyond bias, is tacked on to the bias amount to respectively reach the start and stop sweep points of the frequency range in which the frequency sweep for seeking a resonant frequency is conducted. Once the resonant frequency is found, the parts of the hand piece 30 are caused to oscillate at that resonant frequency.

The memory 400 for an ultrasonic surgical hand piece 30 according to the invention is located in the electrical connector which is disposed between the console 10 and the cable 26. The memory device 400 can also be located in one or more locations, including the electrical connector, within the housing of the hand piece 30, or at an in-line location in the cable 26.

In addition to being an EEPROM, the memory 400 can be one or a combination of a Read Only Memory (ROM), Erasable Programmable Read Only Memory (EPROM), Random Access Memory (RAM) or any other volatile memory which is powered by a cell, battery, or capacitor, such as a super capacitor. The memory 400 can also be a Programmable Array Logic (PAL), Programmable Logic Array (PLA), analog serial storage device, sound storage integrated circuit or similar device, or a memory device in conjunction with a numeric manipulation device such as a microprocessor for the purpose of encryption.

Although the invention has been particularly shown and described in detail with reference to the preferred embodiments thereof, the embodiments are not intended to be exhaustive or to limit the invention to the precise forms disclosed herein. It will be understood by those skilled in the art that many modifications in form and detail may be made therein without departing from the spirit and scope of the invention. Similarly, any process steps described herein may be interchangeable with other steps to achieve substantially the same result. All such modifications are intended to be encompassed within the scope of the invention, which is defined by the following claims and their equivalents.

We claim:

1. A system for implementing surgical procedures comprising:
   an ultrasonic surgical hand piece having an end-effector;
   a console having a digital signal processor (DSP) for controlling the hand piece;
   an electrical connection connecting the hand piece and the console; and
   memory disposed in the electrical connection,
   wherein the console sends a drive current to drive the hand piece which imparts ultrasonic longitudinal movement to the end effector; and
   a memory disposed in the electrical connection,
   wherein the console sends a drive current to drive the hand piece which imparts ultrasonic longitudinal movement to the end-effector, reads information stored in the memory to authenticate the hand piece for use with the console, and determines whether operation of the hand piece should be handicapped or disabled based on the information stored in the memory disposed in the electrical connection.

2. The system of claim 1 wherein the information stored in the memory includes a cyclical redundancy check (CRC) code, and the information stored in the memory firmware implemented data.

3. The system of claim 1 wherein the information is an encrypted code, and the hand piece is authenticated for use with the console by decoding a corresponding encryption algorithm in the console and providing for a corresponding data pattern.

4. The system of claim 1 wherein:
   the information stored in the memory includes a handicap limit and a disable limit;
   the console instructs the hand piece to operate in a handicap mode if the system exceeds the handicap limit, and the console disables the hand piece if the system exceeds the disable limit.

5. The system of claim 4 wherein the handicap limit and the disable limit relate to temperature and the handicap mode is appropriate for temperature conditions.

6. The system of claim 4 wherein the handicap limit and the disable limit relate to the number of defective blades found in a time period of operating the hand piece, and the handicap mode is appropriate for the number of defective blade conditions.

7. The system of claim 4 wherein the handicap limit and the disable limit relate to the time the hand piece has been active, and the handicap mode is appropriate for the time conditions.

8. The system of claim 4 wherein the handicap limit and the disable limit relate to the number of activations for the hand piece within a time period, and the handicap mode is appropriate for the number of activation conditions.

9. The system of claim 4 wherein the handicap mode involves one of operations below a certain speed or vibrational frequency, operating below a certain vibrational displacement, and in a limited mode such as coagulation or cutting.

10. The system of claim 1 wherein the memory includes a reprogram code, wherein said DSP reads the reprogram code stored in the memory and alters at least one function of said console based on said reprogram code.

11. The system of claim 10 further comprising storage and upgrade code, wherein said DSP stores the storage and upgrade code which is read with its operating program.

12. The system of claim 11 wherein the reprogram code and the upgrade code are read from a non-volatile memory of a non-hand piece device plugged into the electrical connection.

13. The system of claim 12 wherein said function of said console is a diagnostic hierarchy.

14. The system of claim 12 wherein said function of said console is a duty-cycle.

15. The system of claim 12 wherein said function of said console redefines power level settings.

16. The system of claim 12 wherein said function of said console redefines the console function assigned to a switch.

17. The system of claim 1 wherein the memory includes information which correlates energy level information and corresponding output displacement, wherein the console reads the energy level information and drives the hand piece according to the corresponding output displacement.

18. The system of claim 1 wherein the information stored in the memory includes a start sweep point and a stop sweep point delimiting a frequency range, and wherein a frequency sweep is effected under control of the DSP in the frequency range loaded on the nominal resonate frequency, the start and stop sweep points for detecting a resonant frequency for operating the hand piece.

19. The system of claim 1 wherein the information stored in the memory includes a nominal resonant frequency, a bias amount and a margin amount from which a frequency range is calculated, and wherein a frequency sweep is effected under control of the DSP in the frequency range based on the nominal resonate frequency, bias current and margin current for detecting a resonant frequency for operating the hand piece.

20. The system of claim 1 wherein the memory comprises at least one of an Electrically Erasable Programmable Read Only Memory (EEPROM), Read Only Memory (ROM), Erasable Programmable Read Only Memory (EPROM), Random Access Memory (RAM), Programmable Array Logic (PAL), Programmable Logic Array (PLA), analog serial storage device, sound storage integrated circuit, a memory device in conjunction with a numeric manipulation device including a microprocessor for the purpose of encryption, and volatile memory which is powered by a device consisting of a cell, battery and capacitor.

21. The system of claim 1 wherein the memory is in a location comprising one of the electrical connection, the housing of the hand piece, and an in-line location in a cable connecting the electrical connection with the console and the hand piece.

* * * * *